United States Patent [19]

Näf et al.

[11] 4,371,460
[45] Feb. 1, 1983

[54] BICYCLIC COMPOUNDS AND UTILIZATION THEREOF AS PERFUMING AGENTS

[75] Inventors: Ferdinand Näf, Carouge; Rene Decorzant; Karl H. Schulte-Elte, both of Onex, all of Switzerland

[73] Assignee: Firmenich SA, Geneva, Switzerland

[21] Appl. No.: 335,196

[22] Filed: Dec. 22, 1981

[30] Foreign Application Priority Data

May 22, 1980 [CH] Switzerland .................. 4008/80

[51] Int. Cl.³ .................. C07C 49/557; A61K 7/46
[52] U.S. Cl. .................. 252/522 R; 568/374; 568/346
[58] Field of Search .................. 568/374; 252/522 R

[56] References Cited

U.S. PATENT DOCUMENTS

| | | | |
|---|---|---|---|
| 3,565,915 | 2/1971 | Matsui et al. | 568/374 |
| 4,247,711 | 1/1981 | Verbrugge et al. | 568/374 |
| 4,284,820 | 8/1981 | Sgrier | 568/374 |

FOREIGN PATENT DOCUMENTS 1435887  5/1976  United Kingdom ............... 568/376

*Primary Examiner*—James H. Reamer
*Attorney, Agent, or Firm*—Pennie & Edmonds

[57] ABSTRACT

Kentones of the formula

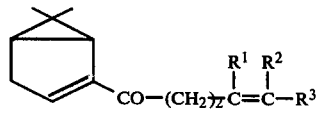

(I)

wherein each of the symbols $R^1$, $R^2$, and $R^3$ identical or different, represent a hydrogen atom or a lower alkyl radical containing 1 to 3 carbon atoms are disclosed useful as perfuming agents and in the preparation of perfume products.

4 Claims, No Drawings

BICYCLIC COMPOUNDS AND UTILIZATION THEREOF AS PERFUMING AGENTS

TECHNICAL FIELD

The present invention relates to the field of perfumery, it reverts more particularly to compounds of formula

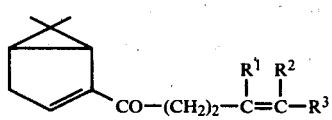

wherein each of symbols $R^1$, $R^2$ and $R^3$, identical or different, represents a hydrogen atom or a lower alkyl radical containing 1 to 3 carbon atoms, preferably a methyl group.

The invention relates also to the utilization of said compounds of formula (I) as perfuming agents for the preparation of perfumes and perfumed products.

DISCLOSURE OF THE INVENTION

Bicyclic ketonic compounds of formula (I) are new chemicals which can be synthesized by means of an original process starting from $\Delta^3$-carene as illustrated by the following scheme.

Scheme:

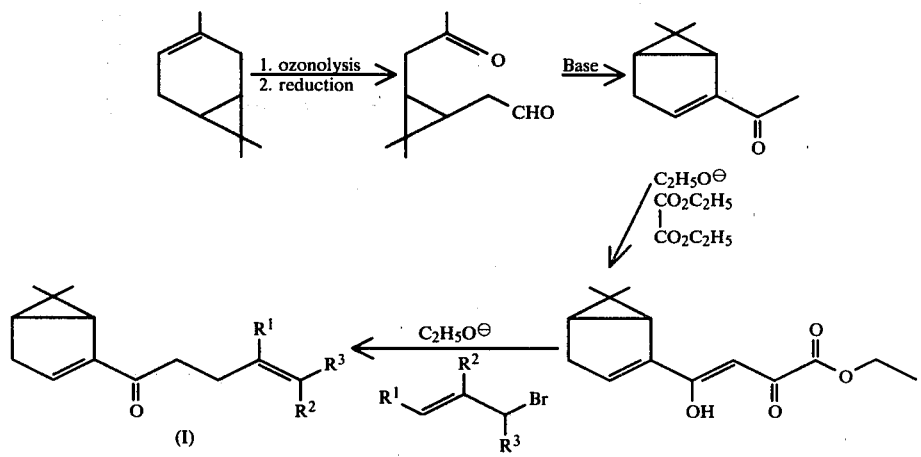

The first two steps of the above process can be carried out in accordance with known methods [see for example British Pat. No. 1,435,887, p. 12] whereas the conversion of 2-acetyl-6,6-dimethyl-bicyclo[3.1.0]hex-2-ene into their derivatives of formula (I) is illustrated in detail in the examples of preparation which follow. In the field of perfumery, compounds of formula (I) are characterized by their original odour of fresh and green type. Their odour characteristic is reminiscent of the green note of galbanum; it is at the same time very rich and especially very flowery and powerful.

Owing to their properties, the compounds of the invention find a very wide utilization for the manufacture of perfume compositions of various nature; moreover, they combine harmoniously with the currently used perfume ingredients. Their utilization is therefore rather broad not only in fine perfumery but also in the perfuming of articles such as soaps, detergents, household materials or cosmetics. The quantities at which the compounds of formula (I) can be used to reproduce interesting perfuming effects vary in a rather wide range of values and depend on the nature of the coingredients in a given perfume composition or on the effect sought. Quantities of the order of 0.5% by weight of the active compound based on the total weight of the composition into which they are incorporated, can already confer a marked effect. Of course, lower proportions, for instance of about 0.1 or 0.2%, can be used for the manufacture of perfumed articles; said values however do not represent absolute limits.

Among the bicyclic compounds of the invention it is worthwhile particularly to mention the following ones:
2-[pent-4-en-1-oyl]-6,6-dimethyl-bicyclo[3.1.0]hex-2-ene,
2-[hex-4-en-1-oyl]-6,6-dimethyl-bicyclo[3.1.0]hex-2-ene,
2-[4-methyl-pent-4-ene-1-oyl]-6,6-dimethyl-bicyclo[3.1.0]hex-2-ene, and
2-[5-methyl-hex-4-en-1-oyl]-6,6-dimethyl-bicyclo[3.1.0]hex-2-ene.

The invention shall be illustrated in a more detailed manner by the following examples. In the said examples, the temperatures are indicated in degrees centigrade and the abbreviations have the sense usual in the art.

EXAMPLE 1

Preparation of
2-[pent-4-ene-1-oyl]-6,6-dimethyl-bicyclo[3.1.0]hex-2-ene (a) A mixture of 15 g (0.1 M) of 2-acetyl-6,6-dimethyl-bicyclo[3.1.0]hex-2-ene and 21.9 g (0.15 M) of diethyloxalate have been added at $-10°/-15°$ to a solution of 2.76 g (0.12 M) of sodium metal in 50 ml of anhydrous ethanol. The reaction mixture was kept under stirring for about 2 hours at room temperature, then it was neutralized with a 10% aqueous solution of HCl. Upon extraction with diethyl ether and separation of the organic phases, followed by drying and evaporation, there were obtained 27.3 g of a residue which by distillation gave 11.7 g of 6,6-dimethyl-2-[2-hydroxy-3-oxo-3-carbethoxy-prop-1-en-1-yl]-bicyclo[3.1.0]hex-2-ene having b.p. 140°/0.5 Torr.

(b) 7.73 g (0.031 M) of the product obtained under letter (a) have been added at room temperature to a solution of 0.86 g (0.037 M) of sodium metal in 30 ml of anhydrous ethanol and the resulting solution was kept under stirring at 25°-30° for 10 minutes. A solution of 3.7 g (0.031 M) of allyl bromide in 15 ml ethanol was then added to the mixture obtained and the whole has been stirred during 20 hours at 75°.

After evaporation of the volatile parts, addition of water and extraction with diethyl ether, followed by the usual treatments, there were obtained 6.45 g of a residue which upon fractional distillation yielded a fraction having b.p. 115°-120°/10 Torr. By purification of this fraction by means of column chromatography with a support of $SiO_2$ there were obtained 3.33 g (yield 56.7%) of the desired product (eluent: hexane/diethyl ether: 98/2). The analytical characteristics of which were the following:

MS:m/e=190 (14), 175 (61), 162 (14), 148 (24), 135 (100), 119 (44), 107 (52), 91 (78), 79 (34), 65 (43), 55 (68), 43 (35), 29 (26);

NMR (60 MHz, $CDCl_3$): 0.75 (3H, s); 1.10 (3H, s); 1.39 (1H, dxd, $J_1=J_2=7$ Hz); 2.00-2.89 (7H, m); 4.96 (1H, d, J=11 Hz); 5.02 (1H, d, J=17 Hz); 5.55-6.10 (1H, m); 6.50 (1H, t) δ ppm.

2-Acetyl-6,6-dimethyl-bicyclo[3.1.0]hex-2-ene, used as starting material in the above described process, can be obtained in accordance with the methods described in British Pat. No. 1,435,887 or according to Agric. Biol. Chem. 31, 33 (1967). The other compounds of formula (I), according to the invention can be obtained by an analogous process, allyl bromide being replaced by the corresponding alkenyl bromide.

The thus prepared products showed the following analytical characteristics:

2-[hex-4-en-1-oyl]-6,6-dimethyl-bicyclo[3.1.0]hex-2-ene

NMR (60 MHz): 0.75 (3H, s); 1.10 (3H, s); 1.37 (1H, dxd, $J_1=7$ Hz; $J_2=7$ Hz); 1.67 (3H, m); 2.00-2.86 (7H, m); 5.38-5.55 (2H, m); 6.49 (1H, m) δ ppm;

MS: $M^+=204$ (39); m/e: 189 (65), 175 (32), 161 (24), 149 (14), 135 (100), 119 (42), 107 (61), 93 (74), 91 (79), 85 (43), 65 (50), 55 (63), 41 (64), 29 (45).

2-[4-methyl-pent-4-en-1-oyl]-6,6-dimethyl-bicyclo[3.1.0]-hex-2-ene

NMR (90 MHz): 0.76 (3H, s); 1.11 (3H, s); 1.38 (1H, dxd, $J_1=7$ Hz, $J_2=7$ Hz); 1.74 (3H, s); 2.04-2.86 (7H, m); 4.66 (1H, s); 4.70 (1H, s); 6.48 (1H, s) δ ppm;

MS: $M^+=204$ (10); m/e: 189 (30), 176 (10), 162 (17), 147 (10), 135 (100), 119 (34), 107 (43), 93 (60), 91 (74), 79 (32), 65 (45), 55 (31), 41 (77).

2-[5-methyl-hex-4-en-1-oyl]-6,6-dimethyl-bicyclo[3.1.0-]hex-2-ene

NMR (90 MHz): 0.76 (3H, s); 1.11 (3H, s); 1.38 (1H, dxd, $J_1=7$ Hz, $J_2=7$ Hz); 1.64 (3H, s); 1.69 (3H, s); 2.04-2.86 (7M, m); 5.09 (3H, t, J=7 Hz); 6.45 (1H, s) δ ppm;

MS: $M^+=218$ (39); m/e: 203 (19), 189 (1), 175 (30), 161 (3), 150 (37), 135 (55), 121 (11), 107 (45), 91 (56), 79 (24), 69 (65), 55 (32), 41 (100).

EXAMPLE 2

Perfuming of soap

A commercial soap paste was perfumed by adding thereto 0.1% by weight of the compound of formula (I) ($R^1=R^2=R^3=H$), and by means of the thus perfumed paste there was prepared toilet soap in accordance with the current technics. The products thus obtained possessed a green and pleasant odorous note.

EXAMPLE 3

Perfuming of a detergent powder

A commercial detergent powder having a bland odour was perfumed of means of the compound of formula (I) ($R^1=R^2=R^3=H$), at a concentration of 0.05% by weight. The resulting product possessed an agreeable odour of green-flowery type.

EXAMPLE 4

Cologne

By adding to a sample of classical cologne 0.1% of the compound of formula (I) ($R^1=R^2=R^3=H$), there was obtained a composition possessing a clinging odour and an enriched floral character.

EXAMPLE 5

Perfuming composition for shampoos

A perfuming composition for shampoos was prepared by mixing the following ingredients (parts by weight):

| | |
|---|---|
| Benzyl salicylate | 200 |
| Phenyl ethanol | 100 |
| Benzyl acetate | 80 |
| Isononyl acetate | 80 |
| Brazilian rose wood oil | 60 |
| Heliotropine | 50 |
| Hydroxycitronellal | 50 |
| Geranyl acetate | 40 |
| Geraniol | 40 |
| Undecenal 10%* | 40 |
| Amylcinnamaldehyde | 30 |
| 1,1-Dimethyl-4-acetyl-6-tert-butyl-indane | 30 |
| α-Isomethylionone | 30 |
| α-DORINONE® 10%*[1] | 20 |
| Styrallyl acetate | 20 |
| Ethyl cyclopentylidene acetate 1%* | 20 |
| Decanal 10%* | 20 |
| Amyl salicylate | 20 |
| Cyclosal | 20 |
| HEDIONE®[1] | 20 |
| DORICENONE® 1%*[1] | 10 |
| Anisaldehyde | 5 |
| MAYOL®[1] | 5 |
| Total | 990 |

*in diethyl phthalate
[1]origin: FIRMENICH SA, Geneva

By adding to this composition of "flowery" type, 10 g (=1%) of the compound of formula (I) ($R^1=R^2=R^3=H$), there was obtained a novel composition whose odour character, more clinging and richer, possessed a green nuance of galbanum type. By using in accordance with Examples 2 to 5 one of the homologous compounds of formula (I) mentioned in Example 1, analogous effects are observed. These however, were less pronounced in the case of the utilization of 2-[5-methyl-hex-4-en-1-oyl]-6,6-dimethyl-bicyclo[3.1.0]hex-2-ene.

We claim:

1. A compound of formula (I)

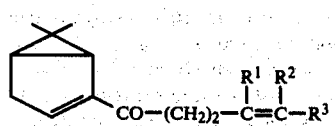

(I)

wherein each of symbols $R^1$, $R^2$ and $R^3$, identical or different, represents a hydrogen atom or a lower alkyl radical having 1 to 3 carbon atoms, preferably a methyl group.

2. Utilization of at least one of the compounds of formula (I) according to claim 1 as perfuming agent for the preparation of perfumes and perfumed products.

3. Perfuming composition characterized in that it contains as active ingredient at least one of the compounds of formula (I) according to claim 1.

4. A perfumed product resulting from the utilization according to claim 2.

* * * * *